(12) United States Patent
Choi

(10) Patent No.: US 7,662,872 B2
(45) Date of Patent: Feb. 16, 2010

(54) SALT OF CARBOXYLIC ACID CONTAINING N-SUBSTITUTED SUCCINIMIDE THIO GROUP AND UNVULCANIZED RUBBER COMPOSITION CONTAINING THE SAME

(75) Inventor: Wonmun Choi, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 487 days.

(21) Appl. No.: 11/545,489

(22) Filed: Oct. 11, 2006

(65) Prior Publication Data

US 2007/0082984 A1   Apr. 12, 2007

(30) Foreign Application Priority Data

Oct. 11, 2005   (JP)   ............................. 2005-296241

(51) Int. Cl.
*C08K 5/16* (2006.01)
(52) U.S. Cl. ......................................... 524/81; 524/418
(58) Field of Classification Search ................. 524/418, 524/81
See application file for complete search history.

(56) References Cited

FOREIGN PATENT DOCUMENTS

| EP | 0 535 470 A1 * | 4/1993 |
|---|---|---|
| JP | 2004-277705 A | 10/2004 |
| WO | WO-96/07655 | 3/1996 |
| WO | WO-03/040133 | 5/2003 |
| WO | WO-2004/074250 | 9/2004 |

OTHER PUBLICATIONS

Marrian, Reactions of the Substituted Maleimides With Thiols, Journal of the Chemical Society, (1949) 1515-16 (Abstract).*
Combrisson et al., Carbon-13 NMR Study of Maleimides and Isomaleimides and Their Thiol Addition Derivatives, Bulletin de la Societe Chimique de France (1975) (11-12, pt. 2), 2769-70 (Abstract).*

* cited by examiner

*Primary Examiner*—Robert D. Harlan
(74) *Attorney, Agent, or Firm*—Connolly Bove Lodge & Hutz LLP

(57) ABSTRACT

A salt of carboxylic acid containing N-substituted succinimide thio group having the formula (I):

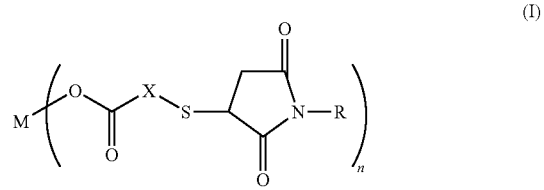

wherein R is a $C_1$ to $C_{20}$ organic group selected from the group consisting of alkyl groups, cycloalkyl groups, aryl groups, and alkaryl groups; X is a $C_1$ to $C_{20}$ organic group selected from the group consisting of alkylene groups, cycloalkylene groups, arylene groups, alkarylene groups, and heterocyclic groups, X may have a substituent group or groups; M is a metal selected from the group consisting of alkaline metal, alkaline earth metal and transition metals belonging to Groups IB and IIB of the Periodic Table; n is equal to the absolute value of the ionic value of the metal M and an integer of 1 or 2.

4 Claims, No Drawings

SALT OF CARBOXYLIC ACID CONTAINING N-SUBSTITUTED SUCCINIMIDE THIO GROUP AND UNVULCANIZED RUBBER COMPOSITION CONTAINING THE SAME

CROSS-REFERENCE TO RELATED APPLICATIONS

This application claims priority from Japanese Application 2005-296241, filed Oct. 11, 2005.

TECHNICAL FIELD

The present invention relates to a novel salt of carboxylic acid containing N-substituted succinimide thio group and an unvulcanized rubber composition containing the same.

BACKGROUND ART

In general, it is known that, when a diene-based rubber is cross-linked (or vulcanized) with sulfur, its cross-linked bonds are mainly composed of polysulfide bonds, which easily break down due to heat, and is known to be inferior in heat aging resistance. On the other hand, butyl rubber is superior to a conventional diene-based rubber in heat aging resistance, but there are few reactive portions, which can be utilized for the vulcanization reaction, and therefore compared to a diene-based rubber, has the problems that it is slow in vulcanization reaction and has difficulty in covulcanization with other diene-based rubber. In view of these problems, as a vulcanization agent or covulcanization agent, a compound composed of a thiol/maleimide adduct having an active hydrogen-containing group which, upon heating, release a maleimide compound and generates a thiol group has already been proposed (see Japanese Patent Publication (A) No. 2004-277705). When the compound disclosed in this patent document is used as a vulcanization agent or covulcanization agent for a butyl rubber, the unvulcanized rubber exhibits a high storage stability and the rubber obtained by vulcanization exhibits a high heat stability.

However, it is still considered necessary to prevent or delay scorching of the unvulcanized rubber composition and further improve the tensile properties and heat aging resistance of the vulcanized rubber.

DISCLOSURE OF THE INVENTION

Accordingly, the object of the present invention is to provide a compound capable of preventing or delaying scorching of an unvulcanized rubber composition and of efficiently increasing the efficiency of the vulcanization reaction of unvulcanized rubber composition so as to further improve the tensile properties and heat aging resistance of the vulcanized rubber obtained and an unvulcanized rubber composition including the same.

In accordance with the present invention, there is provided a salt of carboxylic acid containing N-substituted succinimide thio group having the formula (I):

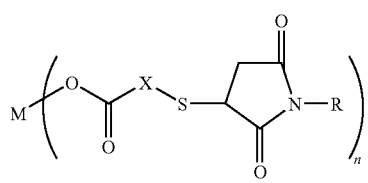

wherein R is a $C_1$ to $C_{20}$ organic group selected from the group consisting of alkyl groups, cycloalkyl groups, aryl groups and alkaryl groups; X is a $C_1$ to $C_{20}$ organic group selected from the group consisting of an alkylene groups, cycloalkylene groups, arylene groups, alkarylene groups and heterocyclic groups, X may further have a substituent group or groups; M is a metal selected from the group consisting of alkaline metals, alkaline earth metals and transition metals belonging to Groups IB and IIB of the Periodic Table; n is equal to the absolute value of the ionic value of the metal M and an integer of 1 or 2.

The present invention, in a first aspect, provides an salt of carboxylic acid containing N-substituted succinimide thio group capable of increasing the vulcanization efficiency of the rubber composition in the vulcanization temperature range and of improving the tensile properties and heat aging resistance of the vulcanized rubber obtained.

The present invention provides, as a second aspect, an unvulcanized rubber composition containing the above salt of carboxylic acid containing N-substituted succinimide thio group.

BEST MODE FOR CARRYING OUT THE INVENTION

In this specification and in the claims which follow, the singular forms "a", "an" and "the" include plural referents unless the context clearly dictates otherwise.

The inventor engaged in intensive studies to solve the above problem and as a result found that, by employing as the vulcanization agent of a rubber composition, a salt of carboxylic acid having the above formula (I)

It is possible to increase the scorch time over a corresponding carboxylic acid and possible to increase the vulcanization efficiency of the rubber composition in the vulcanization temperature range and improve the heat aging resistance of the vulcanized rubber obtained and the tensile properties at room temperature and high temperature and thereby completed the present invention.

The salt of carboxylic acid containing N-substituted succinimide thio group (i.e., a metal salt of the salt of carboxylic acid containing N-substituted succinimide thio group) of the present invention has the formula (I):

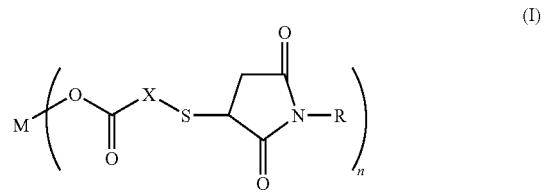

wherein R is a $C_1$ to $C_{20}$ organic group selected from the group consisting of alkyl groups, cycloalkyl groups, aryl groups, and alkaryl groups; X is a $C_1$ to $C_{20}$ organic group selected from the group consisting of alkylene groups, cycloalkylene groups, arylene groups, alkarylene groups, and heterocyclic groups, X may further have a substituent group or groups; M is a metal selected from the group consisting of alkaline metals, alkaline earth metals and transition metals belonging to Groups IB and IIB of the Periodic Table; n is equal to the absolute value of the ionic value of the metal M and an integer of 1 or 2.

In the above general formula (I), R is a $C_1$ to $C_{20}$ organic group selected from the group consisting of alkyl groups, cycloalkyl groups, aryl groups and alkaryl groups and X is a $C_1$ to $C_{20}$ organic group selected from the group consisting of alkylene groups, cycloalkylene groups, arylene groups, alkarylene groups, and heterocyclic groups and may further have a substituent group or groups. In this specification, "alkyl group" means a monovalent linear or branched chain saturated hydrocarbon group. Further, "cycloalkyl group" means a monovalent cyclic saturated hydrocarbon group. An "aryl group" indicates a monovalent monocyclic or polycyclic aromatic hydrocarbon group. An "alkaryl group" means a monovalent group including both an aliphatic hydrocarbon moiety and an aromatic hydrocarbon moiety. An "alkylene group" means a bivalent linear or branched chain saturated hydrocarbon group. A "cycloalkylene group" means a bivalent cyclic saturated hydrocarbon group. An "arylene group" means a bivalent monocyclic or polycyclic aromatic hydrocarbon group. An "alkarylene group" means a bivalent group including both an aliphatic hydrocarbon moiety and an aromatic hydrocarbon moiety. A "heterocyclic group" means a monocyclic or polycyclic aromatic or nonaromatic heterocyclic group.

Regarding the organic group R, as specific examples of alkyl groups among these organic groups, for example, alkyl groups having 1 to 20 carbon atoms such as a methyl group, ethyl group, n-propyl group, isopropyl group, n-butyl group, isobutyl group, sec-butyl group, tert-butyl group, hexyl group, n-octyl group, n-dodecyl group, stearyl group, etc. may be mentioned. As specific examples of cycloalkyl groups having 3 to 20 carbon atoms such as, for example, a cyclohexyl group etc. may be mentioned. As specific examples of aryl groups having 6 to 20 carbon atoms such as, for example, a phenyl group, naphthyl group, etc. may be mentioned. As specific examples of alkaryl groups having 7 to 20 carbon atoms such as, for example, a benzyl group, phenylethyl group, phenylpropyl group, etc. may be mentioned. Regarding the organic group X, as a specific example of alkylene groups having 1 to 20 carbon atoms such as, for example, a methylene group, ethylene group, propylene group, butylene group, hexylene group, octylene-group, etc. may be mentioned. As specific examples of a cycloalkylene groups having 3 to 20 carbon atoms such as, for example, a cyclohexylene group may be mentioned. As specific examples of an arylene groups having 6 to 20 carbon atoms such as, for example, a 1,2-phenylene group, 1,3-phenylene group, 1,4-phenylene group, biphenyl-4,4'-dyl group, diphenylmethan-4,4'-dyl group, 3,3'-dimethylbiphenyl-4,4'-dyl group, etc. may be mentioned, as specific examples of alkarylene groups having 8 to 20 carbon atoms such as, for example, an o-xylylene group, m-xylylene group, p-xylylene group, etc. may be mentioned, as specific examples of a heterocyclic groups having an heteroatom including nitrogen atom, oxygen atom, sulfur atom and having 5 to 20 carbon atoms, such as, for example, a 1,3,4-thiadiazole group, tetrazole group, pyridilene group, 1,3,5-triazine group, etc. may be mentioned. As specific examples of substituent groups which may be further present in the group X, for example, a $C_1$-$C_{20}$ alkoxy group such as a methoxy group, ethoxy group, a halogen group such as chloro group, bromo group, or hydroxy group, etc. may be mentioned. As specific examples of the metal M selected from the group, consisting of an alkaline metal, alkaline earth metal, and transition element of the group IB and IIB of the Periodic Table, for example, sodium, potassium, magnesium, calcium, zinc, copper, silver, etc. may be mentioned.

Specific examples of the compound having the formula (I) are, for example, metal salts of

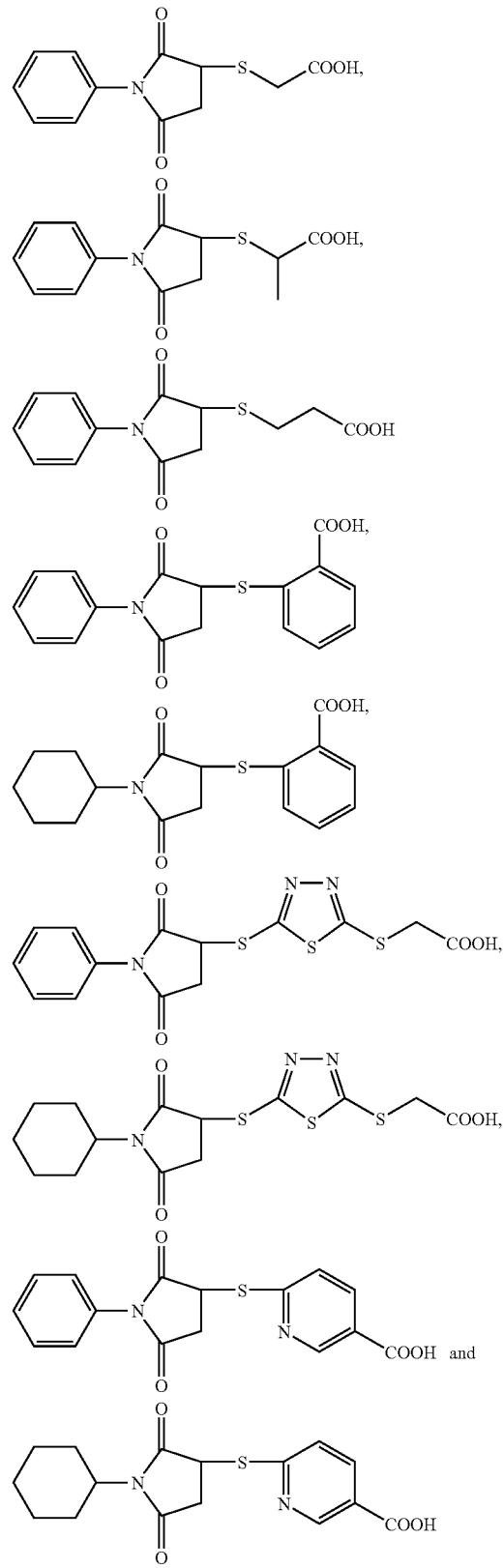

A salt of carboxylic acid containing N-substituted succinimide thio group according to the first aspect of the present invention can, for example, be obtained by a salt forming reaction of the corresponding carboxylic acid. For example, an N-substituted succinimide thio group-containing carboxylic acid having the formula (II):

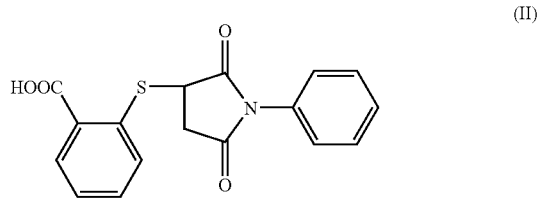

wherein R and X are the same as defined above for the above general formula (I)) and metal hydroxides such as NaOH, KOH, Mg(OH)$_2$, Ca(OH)$_2$, metal oxides such as, MgO, CaO, ZnO, AgO, CuO, or metal halides such as MgBr$_2$, MgCl$_2$, CaBr$_2$, CaCl$_2$, ZnCl$_2$, ZnBr$_2$ may be reacted to obtain a compound having the above formula (I). Among these, due to the high reactivity and ease of formation of a salt with a carboxylic acid, the use of a magnesium compound is preferred. At the time of the reaction, it is desirable to use a metal hydroxide or metal oxide in a equal molar amount to that of the N-substituted succinimide thio group-containing carboxylic acid or a stoichiochemically excess amount. The reaction conditions generally changed depending on the desired product and the type of the raw material. As a solvent, water or an alcohol such as methanol, ethanol, propanol, ethylene glycol, and other solvents such as acetone, methylethylketone, N-methyl-2-pyrrolidone, tetrahydrofuran, N,N-dimethylformamide, toluene, xylene, pentane, hexane, etc. may be used alone or in any combination thereof. The preferable solvents, due to their relative ease of separation from the reaction product, are methanol, ethanol, and propanol. The reaction temperature of the reaction is preferably approximately within the range of 0° C. to approximately 130° C. If the temperature is less than 0° C., the reaction time becomes longer, while the temperature is more than 130° C. reaction temperature, there is a possibility of a remarkable decomposition reaction of the product or unpreferable secondary reaction.

The unvulcanized rubber composition according to the second aspect of the present invention comprises of a predetermined amount of the above salt of carboxylic acid containing N-substituted succinimide thio group and an unvulcanized rubber ingredient selected from the group consisting of a diene-based rubber and halogenated rubber. The specific examples of the diene-based rubber include, for example, natural rubber, butadiene rubber, isoprene rubber, chloroprene rubber, styrene-butadiene copolymer rubber, ethylene-propylene-diene copolymer rubber or acrylonitrile-butadiene copolymer rubber. Further, the specific examples of a halogenated rubber include, for example, halogenated butyl rubber such as brominated butyl rubber, chlorinated butyl rubber, halide of an isobutylene-paramethylstyrene copolymer (for example, bromide), chloroprene rubber, epichlorohydrin rubber, chlorosulfonated polyethylene, chlorinated polyethylene, maleic acid modified chlorinated polyethylene, chlorinated acryl rubber, fluororubber, or an acryl rubber obtained by copolymerization of halogen-based monomers.

In an unvulcanized rubber composition according to the second aspect of the present invention, the salt of carboxylic acid containing N-substituted succinimide thio group according to the first aspect of the present invention may be used alone, without using another vulcanization agent and/or vulcanization accelerator. However, so long as the desired vulcanization and/or vulcanization acceleration effect is achieved, without inhibiting the vulcanization and/or vulcanization acceleration action of the salt of carboxylic acid containing N-substituted succinimide thio group and, therefore, the improvement in the tensile properties and heat aging resistance can be achieved, it is possible to use the present salt of carboxylic acid containing N-substituted succinimide thio group, in combination with other vulcanization agent and/or vulcanization accelerator included in the rubber vulcanization compounding agent. The other vulcanization agent and/or vulcanization accelerator desirably also has not a detrimental effect on the scorch time. The compound according to the first aspect of the present invention may be used in any ratio to the total amount of the other vulcanization agent and/or vulcanization accelerator. However, to achieve the desired vulcanization and/or vulcanization acceleration effect, 0.2 to 20 parts by weight, based upon 100 parts by weight of the unvulcanized rubber ingredient selected from the group consisting of a diene-based rubber and halogenated rubber. If the amount of the salt of carboxylic acid containing N-substituted succinimide thio group is in this range, more advantageous effects such as realization of a practical strength and rubber elasticity can be obtained.

When a conventional carboxylic acid proposed as a vulcanization agent or covulcanization agent is used, in order for the carboxylic acid to act as a vulcanization agent or co-vulcanization agent, it is believed to be necessary that to go through a process of forming a salt once by the reaction of the carboxylic acid and metal oxide such as zinc oxide generally known as a vulcanization agent or vulcanization accelerator and/or acid receiver or stabilizer. It is believed that the carboxylate group produced by this salt forming reaction reacts with the other reactive sites of the rubber ingredient such as the halogen groups. On the other hand, the compound of the present invention is already in the form of a carboxylate salt, and therefore, the activity to a substitution reaction with the halogen groups, etc. of the rubber ingredient is high. Further, no reaction with an additive separately added, such as zinc oxide, magnesium oxide, is required, so the reaction efficiency of the substitution reaction with the rubber ingredient is believed to be high. Therefore, regarding the later maleimide disassociation reaction of the next step as well, the reaction efficiencies of the substitution reactions of the prior and later stages are high, and therefore, the reaction efficiency to the amount of said carboxylate added high. As a result, it is believed that tensile properties and heat aging resistance are improved over those, in the case where of an equal molar amount of the corresponding carboxylic acid are used, can be achieved. Further, when a salt of the corresponding carboxylic acid is used, it is possible to not use or to reduce the amount of use of the vulcanization agent or vulcanization acceleration aid separately added to the rubber composition in the past and to achieve the improvement in the tensile properties and heat aging resistance. In particular, when the salt of carboxylic acid containing N-substituted succinimide thio group of the present invention is a zinc salt, magnesium salt or calcium salt, it is possible to reduce the addition amount of the zinc oxide, magnesium oxide, or calcium hydroxide generally known to be useful as a vulcanization agent or vulcanization acceleration aid and/or acid acceptor or stabilizer and to achieve the improvement in the tensile properties and heat aging resistance.

When the salt of carboxylic acid containing N-substituted succinimide thio group of the present invention is used in a diene-based rubber composition, like in the existing corresponding carboxylates, the bonds between the thio groups and N-substituted succinimide groups are cleavaged by heat, whereby N-substituted maleimide release. The thiol groups produced simultaneously with this reaction exhibit a vulcanization acceleration effect. Further, when the salt of carboxylic acid containing N-substituted succinimide thio group is used for a bromobutyl rubber composition or other halogenated rubber composition, the salt of carboxylic acid containing N-substituted succinimide thio group of the present invention already has carboxylate groups activated by the presence of the metal ions, and therefore, even if there is no zinc oxide or other vulcanization accelerator present, the halogen groups in the rubber molecules are easily substituted in the reaction. The substitution reaction with the halogen groups in the rubber molecules can partially occur during the mixing of the rubber composition before vulcanization. The compound of the present invention reacts with the halogen groups, then normal vulcanization cleaves the S—C bonds between the thio groups and the N-substituted succinimide groups. The thiol groups produced by the cleavage of the S—C bonds between the thio group and the N-substituted succinimide groups act as a vulcanization accelerator and vulcanization agent in the presence of a vulcanization agent. Even when there is no vulcanization agent present, a salt is formed from the reaction with the zinc oxide in the rubber composition. By a direct reaction with the halogen groups of the rubber molecules, the salt of carboxylic acid containing N-substituted succinimide thio group functions as a vulcanization agent.

The unvulcanized rubber composition of the present invention may contain therein a vulcanization agent and vulcanization accelerator other than the above vulcanization agent and vulcanization accelerator, reinforcing agents usually compounded into a rubber composition, such as carbon black, silica, vulcanization acceleration aids such as stearic acid, various types of oil, fillers, paraffin oil such as softening agents, plasticizers, surfactants, antistatic agents, antioxidants and other compounding agents and additives in amounts generally used according to the applications by general compounding methods. The salt of carboxylic acid containing N-substituted succinimide thio group of the present invention may be used in any ratio to the total amount of the other vulcanization agent and/or vulcanization accelerator contained in the rubber vulcanization compounding agents so long as the desired improvement in the vulcanization and/or vulcanization acceleration effect and tensile properties and heat aging resistance can be obtained.

Specific examples of the vulcanization agent usable in the unvulcanized rubber composition, in combination with the salt of carboxylic acid containing N-substituted succinimide thio group of the present invention, are for example, sulfur, an organic peroxide, quinone dioxime, metal oxide, alkyl phenol-formaldehyd resin, etc. Further, the present unvulcanized rubber composition preferably includes a sulfenamide-based or thiuram-based vulcanization accelerator. By using a sulfonamide-based or thiuram-based vulcanization accelerator, vulcanization of the rubber ingredient is further accelerated and, further, the physical properties of the vulcanized rubber obtained can be further improved. As a sulfenamide-based vulcanization accelerator, for example, an N-cyclohexyl-2-benzothiazolyl sulfenamide, N-t-butyl-2-benzothiazolyl sulfenamide, N-oxydiethylene-2-benzothiazolyl sulfenamide or N,N'-dicyclohexyl-2-benzothiazolyl sulfenamide may be mentioned. As a thiuram-based vulcanization accelerator, for example, a tetrakis(2-ethylhexyl)thiuram disulfide, tetramethylthiuram disulfide, tetraethylthiuram disulfide, tetramethylthiuram monosulfide, tetrabenzylthiuram disulfide or dipentamethylenethiuram tetrasulfide may be mentioned.

The present composition is mixed by a conventional rubber mixer such as a roll, Banbury mixer, kneader, etc.

The unvulcanized rubber composition of the present invention may be used for various adhesives, tackifiers, coating agents, sealing agents, etc.

EXAMPLES

The present invention will now be explained in further detail with reference to the Examples and Comparative Examples shown below, but the present invention is by no means limited to these Examples.

1) Synthesis of Salt of Carboxylic Acid Containing N-Substituted Succinimide Thio Group 30.8 g (0.20 mol) of thiosalicyclic acid and 34.6 g (0.20 mol) of N-phenylmaleimide were reacted in 300 g of methylethylketone at 90° C. for 5 hours. After the end of the reaction, the reaction mixture is concentrated under reduced pressure at 90° C. to obtain 65.0 g (yield 99%) of the compound (molecular weight 327.4) (hereinbelow, referred to as the "compound 1") having the following formula:

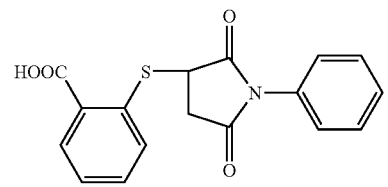

Next, a 300 ml three-neck round-bottom flask provided with a thermometer and a magnetic stirrer was charged with 70 g of methanol and 32.7 g (0.10 mol) of the compound 1 and 2.22 g (0.055 mol) of magnesium oxide which were then reacted at 70° C. for 2 hours. Thereafter, the reaction mixture was concentrated at 70° C. in vacuo so as to obtain the compound having the following formula (i.e., compound 2, molecular weight 677.0) in an amount of 33.2 g (yield 98%).

2) Identification of Salt of Carboxylic Acid Containing N-Substituted Succinimide Thio Group The product obtained as explained above was analyzed by $^1$H-nuclear magnetic resonance spectrometry ($^1$H-NMR) and mass spectrometry (MS). The $^1$H-NMR spectrum and MS spectrum thus obtained were as follows:

$^1$H-NMR spectrum (DMSO-$d_6$): 2.7 ppm (CH$_2$, 1H), 3.5 ppm (CH$_2$, 1H), 4.7 ppm (S—CH, 1H), 7.2 to 7.7 ppm (Ph, 9H).

FAB-MS spectrum [M+H]$^+$: 677, measured using JMS-BU20 GC Mate made by Nihon Denshi Datum under high speed xenon atomic beam From the results, the above product was identified as having a chemical structure expressed by the following formula:

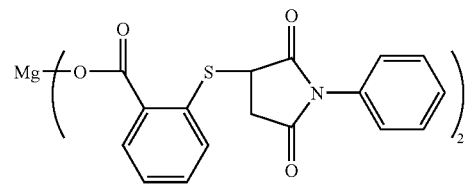

This product will be called the compound 2 herein below.

3. Preparation of Unvulcanized Rubber Composition

The ingredients of the formulation shown in the following Table I were mixed in a 1.8 liter Banbury mixer for 5 minutes to homogeneously disperse them and obtain an unvulcanized rubber composition of Examples and Comparative Examples. The Examples and Comparative Examples of an unvulcanized rubber composition obtained were evaluated by the test methods explained below. Note that the formulations were determined so that the mole number of the compound 1 used in Comparative Example 2 and the mole number of carboxylic acid included in the compound 2 used in Example 1 are substantially equal.

TABLE I

Formulation of Rubber Composition

| | Formulation (parts by weight) | | |
|---|---|---|---|
| Ingredient | Comp. Ex. 1 | Comp. Ex. 2 | Ex. 1 |
| Brominated butyl rubber[1] | 100.00 | 100.00 | 100.00 |
| Carbon black[2] | 60.00 | 60.00 | 60.00 |
| Oil[3] | 11.00 | 11.00 | 11.00 |
| Stearic acid[4] | 1.00 | 1.00 | 1.00 |
| Zinc oxide[5] | 3.00 | 3.00 | 3.00 |
| Vulcanization accelerator[6] | 1.05 | 0 | 0 |
| Sulfur[7] | 0.53 | 0 | 0 |
| Compound 1 | 0 | 2.80 | 0 |
| Compound 2 | 0 | 0 | 3.00 |

Notes:
[1] Made by Bayer Polysar B.N.Y
[2] GPF carbon black made by Mitsubishi Chemical
[3] Paraffin oil made by Showa Shell Oil
[4] Made by NOF Corporation
[5] Made by Seido Chemical
[6] Noccelar DM made by Ouchi Shinko Chemical Industries
[7] Fine powder sulfur made by Tsurumi Chemical Industry 4. Test Methods (1) Mooney Scorch Time:

The unvulcanized rubber compositions obtained above were continuously determined for Mooney viscosity according to JIS K6300-1994 using an L-rotor and under conditions of a preheating time of 1 minute and a test temperature of 125° C. The minimum value of the Mooney viscosity was made $V_m$, and the Mooney scorch time (min) until the Mooney viscosity increased 5 points from $V_m$ was found. The results are shown in Table II. The Mooney scorch time is an indicator of scorching (rubber scorching). The larger the value, the better the result.

(2) Compression Set:

The unvulcanized rubber compositions obtained above were vulcanized at 148° C. for 30 minutes or 180° C. for 10 minutes to prepare cylindrical test pieces (diameter 29 mm×thickness 12.5 mm). The cylindrical test pieces were compressed 25% according to JIS K6262, allowed to stand at 70° C. for 22 hours, then determined for compression set. The smaller the value, the better the result.

(3) Tensile Properties:

The unvulcanized rubber compositions thus obtained were vulcanized at 148° C. for 30 minutes or 180° C. for 10 minutes to prepare 15 cm×15 cm×2 mm vulcanized sheets. JIS No. 3 dumbbell shaped test pieces were punched out from these vulcanized sheets. Next, according to JIS K6251, the modulus at the time of 100% elongation (M100), modulus at the time of 300% elongation (M300), tensile stress at break ($T_B$) and elongation at break ($E_B$) were found and those values were used as initial values. Further, other samples of the unvulcanized rubber compositions were vulcanized at 148° C. for 30 minutes or 180° C. for 10 minutes, then were aged according to JIS K6257 at 100° C. for 96 hours and measured for M100, M300, $T_B$ and $E_B$. Further, still other samples of the above unvulcanized rubber compositions were vulcanized at 148° C. for 30 minutes, were then measured at 100° C. according to JIS K6251 for the M100, M300, $T_B$ and $E_B$. For the M100 and M300, the rates of change (%) in the values after aging based on the above initial values were found according to the following formulae:

[($M$100 after aging)−($M$100 before aging)]×100/
($M$100 before aging)

[($M$300 after aging)−($M$300 before aging)]×100/
($M$300 before aging)

The smaller the value of the rate of change, the better the heat aging resistance.

TABLE II

Test Results of Mooney Scorch Time and Compressive Set

| Physical properties | Comp. Ex. 1 | Comp. Ex. 2 | Ex. 1 |
|---|---|---|---|
| Mooney scorch time (min) | 16.3 | 15.2 | 18.2 |
| Compression set (148° C., 30 min vulcanization) | 21.8 | 20.8 | 13.9 |
| Compression set (180° C., 10 min vulcanization) | 22.1 | 27.1 | 15.9 |

TABLE III

Test Results of Tensile Properties

| Physical Properties | Comp. Ex. 1 | Comp. Ex. 2 | Ex. 1 |
|---|---|---|---|
| M100 (MPa) [148° C., 30 min vulcanization] | 1.0 | 1.4 | 1.6 |
| M100 (MPa) [148° C., 30 min vulcanization, then 100° C., 96 hour aging] | 1.4 | 1.6 | 1.7 |
| Rate of change (%) | 40.0 | 14.3 | 6.3 |
| M100 (MPa) [180° C., 10 min vulcanization] | 1.0 | 1.3 | 1.6 |
| M100 (MPa) [180° C., 10 min vulcanization, then 100° C., 96 hour aging] | 1.3 | 1.5 | 1.7 |
| Rate of change (%) | 30.0 | 15.4 | 6.3 |
| M300 (MPa) [148° C., 30 min vulcanization] | 3.0 | 4.0 | 4.5 |
| M300 (MPa) [148° C., 30 min vulcanization, then 100° C., 96 hour aging] | 4.3 | 4.5 | 4.7 |
| Rate of change (%) | 43.3 | 12.5 | 4.4 |
| M300 (MPa) [180° C., 10 min vulcanization] | 3.2 | 3.8 | 4.4 |
| M300 (MPa) [180° C., 10 min vulcanization, then 100° C., 96 hour aging] | 4.2 | 4.3 | 5.0 |
| Rate of change (%) | 31.3 | 13.2 | 13.6 |
| 100° C. M100 (MPa) [148° C., 30 min vulcanization] | 0.6 | 0.8 | 1.0 |
| 100° C. M300 (MPa) [148° C., 30 min vulcanization] | 2.0 | 2.5 | 2.8 |
| $T_B$ [148° C., 30 min vulcanization] | 9.2 | 9.0 | 9.6 |
| $T_B$ [148° C., 30 min vulcanization, then 100° C., 96 hour aging] | 8.7 | 8.4 | 8.6 |
| $T_B$ [180° C., 10 min vulcanization] | 9.2 | 9.2 | 9.9 |
| $T_B$ [180° C., 10 min vulcanization, then 100° C., 96 hour aging] | 8.4 | 8.7 | 9.4 |
| 100° C. $T_B$ [148° C., 30 min vulcanization] | 4.0 | 5.0 | 4.8 |
| $E_B$ [148° C., 30 min vulcanization] | 871 | 825 | 818 |
| $E_B$ [148° C., 30 min vulcanization, then 100° C., 96 hour aging] | 789 | 796 | 761 |
| $E_B$ [180° C., 10 min vulcanization] | 871 | 846 | 850 |
| $E_B$ [180° C., 10 min vulcanization, then 100° C., 96 hour aging] | 784 | 843 | 804 |
| 100° C. $E_B$ [148° C., 30 min vulcanization] | 797 | 847 | 747 |

As will be understood from the results shown in Tables II and III, the salt of carboxylic acid containing N-substituted succinimide thio group of the present invention has a high vulcanization acceleration effect with respect to a diene-based rubber and halogenated butyl rubber and further acts as a vulcanization agent with respect to a halogenated butyl rubber. Further, the vulcanized rubber composition obtained from an unvulcanized rubber composition including an salt of carboxylic acid containing N-substituted succinimide thio group of the present invention exhibits the improved tensile properties and heat aging resistance over those obtained from a conventional unvulcanized rubber composition including a vulcanization agent and/or vulcanization accelerator and exhibits a high resistance to mechanical deformation from the lower value of the compression set.

The invention claimed is:

1. A salt of carboxylic acid containing N-substituted succinimide thio group represented by the following formula (I)

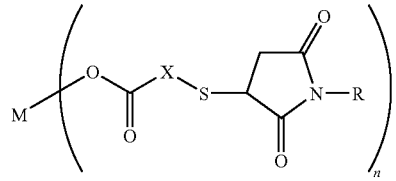

wherein R is a phenyl group; X is a $C_1$ to $C_{20}$ organic group selected from the group consisting of arylene groups and monocyclic or polycyclic aromatic heterocyclic groups, X may further have a substituent group or groups; M is magnesium; n is 2.

2. A salt of carboxylic acid containing N-substituted succinimide thio group represented by the following formula (I)

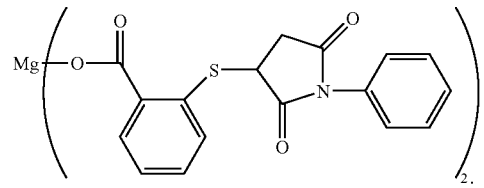

3. An unvulcanized rubber composition comprising an unvulcanized rubber selected from the group consisting of diene-based rubbers and halogenated rubbers including therein the carboxylic acid salt, according to claim 1.

4. An unvulcanized rubber composition comprising an unvulcanized rubber selected from the group consisting of diene-based rubbers and halogenated rubbers including therein the carboxylic acid salt, according to claim 2.

* * * * *